United States Patent
Beers et al.

[11] Patent Number: 5,965,583
[45] Date of Patent: Oct. 12, 1999

[54] SUBSTITUTED IMIDAZOLES USEFUL IN THE TREATMENT OF INFLAMMATORY DISEASE

[75] Inventors: Scott A. Beers; Elizabeth A. Malloy, both of Flemington; Michael P. Wachter, Bloomsbury; Wei Wu, Somerville, all of N.J.

[73] Assignee: Ortho-McNeil Pharmaceutical, Inc., Raritan, N.J.

[21] Appl. No.: 09/062,304

[22] Filed: Apr. 17, 1998

Related U.S. Application Data

[60] Provisional application No. 60/044,252, Apr. 24, 1997.

[51] Int. Cl.⁶ ........................ C07D 401/04; A61K 31/44
[52] U.S. Cl. ........................ 514/341; 546/274.1
[58] Field of Search ................ 546/274.1; 514/341

[56] References Cited

U.S. PATENT DOCUMENTS

| | | | |
|---|---|---|---|
| 4,503,065 | 3/1985 | Wilkerson | 514/396 |
| 4,608,382 | 8/1986 | Ferrini et al. | 514/341 |
| 5,633,377 | 5/1997 | Thurkauf et al. | 546/210 |

FOREIGN PATENT DOCUMENTS

| | | |
|---|---|---|
| 93 14081 | 7/1993 | WIPO . |
| 96 03387 | 8/1996 | WIPO . |

*Primary Examiner*—Jane Fan
*Attorney, Agent, or Firm*—John Harbour

[57] ABSTRACT

This invention relates to a series of substituted imidazoles of Formula I

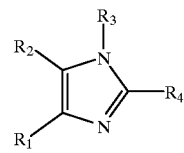

pharmaceutical compositions containing them and intermediates used in their manufacture. The compounds of the invention inhibit the production of a number of inflammatory cytokines, and are useful in the treatment of diseases associated with overproduction of inflammatory cytokines.

17 Claims, No Drawings

SUBSTITUTED IMIDAZOLES USEFUL IN THE TREATMENT OF INFLAMMATORY DISEASE

This application claims the benefit of provisional application 60/044,252 filed Apr. 27, 1997 under 119 (e).

This invention relates to a series of substituted imidazoles, pharmaceutical compositions containing them and intermediates used in their manufacture. The compounds of the invention inhibit the production of a number of inflammatory cytokines, particularly, TNF-α, and IL-1β. Compounds of this invention are useful in the treatment of diseases associated with overproduction of inflammatory cytokines, such as rheumatoid arthritis, inflammatory bowel disease, septic shock, osteoporosis, and osteoarthritis.

BACKGROUND OF THE INVENTION

The inflammatory cytokines, IL-1β and TNF-α play an important role in a number of inflammatory diseases such as rheumatoid arthritis. C. Dinarello et al,. Inflammatory cytokines: Interleukin-1 and Tumor Necrosis Factor as Effector Molecules in Autoimmune Diseases *Curr. Opin. Immunol.* 1991, 3, 941-48. Arthritis is an inflammatory disease which affects millions of people and can strike at any joint of the human body. Its symptoms range from mild pain and inflammation in affected joints, to severe and debilitating pain and inflammation. Although the disease is associated mainly with aging adults, it is not restricted to adults. The most common arthritis therapy involves the use of nonsteroidal antiinflammatory drugs (NSAID) to alleviate the symptoms. However, despite their widespread use, many individuals cannot tolerate the doses necessary to treat the disease over a prolonged period of time. In addition, NSAIDs merely treat the symptoms of disease without affecting the underlying cause. Other drugs, such as methotrexate, gold salts, D-pencillamine, and prednisone are often used when patients fail to respond to NSAIDS. These drugs also have significant toxicities and their mechanism of action remain unknown.

Receptor antagonists to IL-1β and monoclonal antibodies to TNF-α have been shown to reduce symptoms of rheumatoid arthritis in small-scale human clinical trials. In addition to protein based therapies, there are small molecule agents which inhibit the production of these cytokines and have demonstrated activity in animal arthritis models. J. C. Boehm et al., 1-Substituted 4-Aryl-5-pyridinylimidazoles: A New Class of Cytokine Suppressive Drugs With Low 5-Lipoxygenase and Cyclooxygenase Inhibitory Potency, *J. Med. Chem.*, 1996, 39, 3929-37. Of these small molecule agents, SB 203580 has proved effective in reducing the production of TNF-α and IL-1 in LPS stimulated human monocyte cell lines with IC50 values of 50 to 100 nM. J. Adams et al., Imidazole Derivatives And Their Use as Cytokine Inhibitor, International Patent application WO 93/14081, Jul. 23,1993. In addition to this in vitro test, SB 203580 inhibits the production of the inflammatory cytokines in rats and mice at $IC_{50}$ values of 15 to 25 mg/kg. A. M. Badger, et al, Pharmacological Profile of SB 203580, A Selective Inhibitor of Cytokine Suppressive Binding Protein/p38 Kinase, in Animal Models of Arthritis, Bone Resorption, Endotoxin Shock and Immune Function, *The Journal of Pharmacology and Experimental Therapeutics,* 1996, 279, 145361. Although human data is currently unavailable for SB 203580, monoclonal antibodies to TNF-α have proved efficacious in the treatment of rheumatoid arthritis. M. J. Elliot et al., Treatment of Rheumatoid Arthritis with Chimeric Monoclonal Antibodies to Tumor Necrosis Factor α, *Arthritis Rheum.* 1993 36, 1681–90. Due to SB 203580's oral activity and potency in animal models, researchers have suggested that a compound with this profile has potential as a viable treatment for rheumatoid arthritis. A. M. Badger, et al. Pharmacological Profile of SB 203580, A Selective Inhibitor of Cytokine Suppressive Binding Protein/p38 Kinase, in Animal Models of Arthritis, Bone Resorption, Endotoxin Shock and Immune Function, *The Journal of Pharmacology and Experimental Therapeutics,* 1996, 279, 1453–61.

SB 203580 and other small molecule agents reduce the production of inflammatory cytokines by inhibiting the activity of a serine/threonin kinase p38 (note other researchers refer to this enzyme as CSBP), at an $IC_{50}$ of 200 nM. D. Griswold et al., Pharmacology of Cytokine Suppressive Anti-inflammatory Drug Binding Protein (CSPB), A Novel Stress-induced Kinase, *Pharmacology Communications,* 1996, 7, 323–29. Although the precise mechanism of this kinase is unknown, it has been implicated in both the production of TNF-α and the signaling responses associated with the TNF-α receptor.

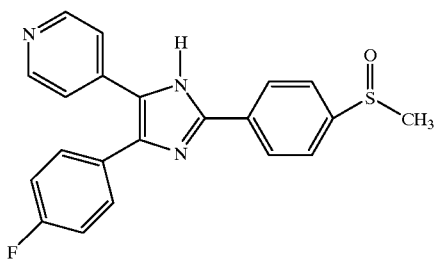

SUMMARY OF THE INVENTION

The novel compounds of this invention inhibit the in vitro activity of p-38 in the nanomolar range. In addition, the compounds inhibit the in vitro secretion of TNF-α and IL-1β in the nanomolar range. Animal models demonstrate the inhibition of LPS induced TNF-α, as well as the inhibition of rheumatoid arthritis. With this range of activity the compounds of the invention are useful in the treatment of a variety of cytokine related disorders including: rheumatoid arthritis, inflammatory bowel disease, septic shock osteoporosis, osteoarthritis, neuropathic pain, HIV replication, HIV dementia, viral myocarditis, insulin-dependent diabetes, non-insulin dependent diabetes, periodontal disease, restenosis, alopecia areta, T-cell depletion in HIV infection or AIDS, psoriasis, acute pancreatitis, allograft rejection, allergic inflammation in the lung, atherosclerosis, mutiple sclerosis, cachexia, alzheimer's disease, stroke, Crohn's disease, inflammatory bowel disease, ischemia, congestive heart failure, pulmonary fibrosis, hepatitis, glioblastoma, Guillain-Barre Syndrome, and systemic lupus erythematosus.

The invention relates to compounds of the Formula I

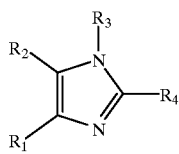

wherein:

$R_1$ is phenyl, substituted phenyl (where the substituents are selected from the group consisting of $C_{1-5}$alkyl, halogen, nitro, trifluoromethyl, and nitrile), or heteroaryl where the heteroaryl contains 5 to 6 ring atoms;

$R_2$ is phenyl, substituted phenyl (where the substituents are selected from the group consisting of $C_{1-5}$alkyl, halogen, nitro, trifluoromethyl, and nitrile), heteroaryl where the heteroaryl contains 5 to 6 ring atoms and is optionally $C_{1-4}$ alkyl substituted;

$R_3$ is hydrogen, SEM, $C_{1-5}$alkoxycarbonyl, aryloxycarbonyl, aryl$C_{1-5}$alkyloxycarbonyl, aryl$C_{1-5}$alkyl, substituted aryl$C_{1-5}$alkyl (where the aryl substituents are independently selected from one or more members of the group consisting of $C_{1-5}$alkyl, $C_{1-5}$alkoxy, halogen, amino, $C_{1-5}$alkylamino, and di$C_{1-5}$alkylamino), phthalimido$C_{1-5}$alkyl, amino$C_{1-5}$alkyl, diamino$C_{1-5}$alkyl, succinimido$C_{1-5}$alkyl, $C_{1-5}$alkylcarbonyl, arylcarbonyl, $C_{1-5}$alkylcarbonyl$C_{1-5}$alkyl, aryloxycarbonyl$C_{1-5}$alkyl, heteroaryl$C_{1-5}$alkyl where the heteroaryl contains 5 to 6 ring atoms;

$R_4$ is —(A)—$(CH_2)_q$—X where
A is vinylene, ethynylene or

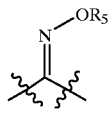

where
$R_5$ is selected from the group consisting of hydrogen, $C_{1-5}$alkyl, phenyl and phenyl$C_{1-5}$alkyl;

q is 0–9;

X is selected from the group consisting of hydrogen, hydroxy, vinyl, substituted vinyl (where one or more substituents are selected from the group consisting of fluorine, bromine, chlorine and iodine), ethynyl, substituted ethynyl (where the substituents are selected from one or more of the group consisting of fluorine, bromine chlorine and iodine), $C_{1-5}$-alkyl, substituted $C_{1-5}$alkyl (where the alkyl substituents are selected from the group consisting of one or more $C_{1-5}$alkoxy trihaloalkyl, phthalimido and amino), $C_{3-7}$cycloalkyl, $C_{1-5}$alkoxy, substituted $C_{1-5}$alkoxy (where the alkyl substituents are selected from the group consisting of phthalimido and amino), phthalimidooxy, phenoxy, substituted phenoxy (where the phenyl substituents are selected from the group consisting of $C_{1-5}$alkyl, halogen and $C_{1-5}$alkoxy), phenyl, substituted phenyl (where the phenyl substituents are selected from the group consisting of $C_{1-5}$alkyl, halogen and $C_{1-5}$alkoxy), aryl$C_{1-5}$alkyl, substituted aryl$C_{1-5}$alkyl (where the aryl substituents are selected from the group consisting of $C_{1-5}$alkyl, halogen and $C_{1-5}$alkoxy), aryloxy $C_{1-5}$alkyl amino, $C_{1-5}$alkylamino, di$C_{1-5}$alkylamino, nitrile, oxime, benxyloxyimino, $C_{1-5}$salkyloxyimino, phthalimido, succinimido, $C_{1-5}$alkylcarbonyloxy, phenylcarbonyloxy, substituted phenylcarbonyoxy (where the phenyl substitutents are selected from the group consisting of $C_{1-5}$alkyl, halogen and $C_{1-5}$alkoxy), phenyl$C_{1-5}$alkylcarbonyloxy, (where the phenyl substitutents are selected from the group consisting of $C_{1-5}$alkyl, halogen and $C_{1-5}$alkoxy), aminocarbonyloxy, $C_{1-5}$alkylaminocarbonyloxy, di$C_{1-5}$alkylaminocarbonyloxy, $C_{1-5}$alkoxycarbonyloxy, substituted $C_{1-5}$alkoxycarbonyloxy (where the alkyl substituents are selected from the group consisting of methyl, ethyl, isopropyl and hexyl), phenoxycarbonyloxy, substituted phenoxycarbonyloxy (where the phenyl substituents are selected from the group consisting of $C_{1-5}$alkyl, $C_{1-5}$alkoxy, and halogen), $C_{1-5}$alkylthio, substituted $C_{1-5}$alkylthio (where the alkyl substituents are selected from the group consisting of hydroxy and phthalimido), $C_{1-5}$alkylsulfonyl, phenylsulfonyl, substituted phenylsulfonyl (where the phenyl substituents are selected from the group consisting of bromine, fluorine, chloride, $C_{1-5}$alkoxy and trifluoromethyl);

with the proviso:
if A is

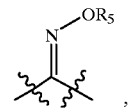

q is 0 and X is H, $R_3$ may not be SEM;
and pharmaceutically acceptable salts thereof.

In addition this invention contemplates pharmaceutical compositions containing compounds of Formula I, and methods of treating cytokine mediated disorders with compounds of Formula I.

Aside from compounds of Formula I, this invention contemplates intermediate compounds of the Formula II. These intermediates are useful in the preparation of compounds of Formula I and are as follows:

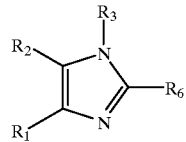

II wherein:
$R_1$ is phenyl, substituted phenyl (where the substituents are selected from the group consisting of $C_{1-5}$alkyl, halogen, nitro, trifluoromethyl, and nitrile), or heteroaryl where the heteroaryl contains 5 to 6 ring atoms;

$R_2$ is heteroaryl where the heteroaryl contains 5 to 6 ring atoms and is optionally $C_{1-4}$ alkyl substituted;

$R_3$ is hydrogen, SEM, $C_{1-5}$alkoxycarbonyl, aryloxycarbonyl, aryl$C_{1-5}$alkyloxycarbonyl, aryl$C_{1-5}$alkyl, substituted aryl$C_{1-5}$alkyl (where the aryl substituents are independently selected from one or more members of the group consisting of $C_{1-5}$alkyl, $C_{1-5}$alkoxy, halogen, amino, $C_{1-5}$alkylamino, and di$C_{1-5}$alkylamino), phthalimido$C_{1-5}$alkyl, amino$C_{1-5}$alkyl, diamino$C_{1-5}$alkyl, succinimido$C_{1-5}$alkyl, $C_{1-5}$alkylcarbonyl, arylcarbonyl, $C_{1-5}$alkylcarbonyl$C_{1-5}$alkyl, aryloxycarbonyl$C_{1-5}$alkyl, heteroaryl$C_{1-5}$alkyl where the heteroaryl contains 5 to 6 ring atoms;

$R_6$ is iodine, chlorine, or bromine; and pharmaceutically acceptable salts thereof.

In addition, this invention contemplates methods of preparing compounds of Formula I.

These methods comprise contacting a compound of Formula III

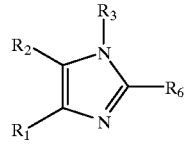

III wherein
$R_1$ is phenyl, substituted phenyl (where the substituents are selected from the group consisting of $C_{1-5}$alkyl, halogen, nitro, trifluoromethyl, and nitrile), or heteroaryl where the heteroaryl contains 5 to 6 ring atoms;

$R_2$ is phenyl, substituted phenyl (where the substituents are selected from the group consisting of $C_{1-5}$alkyl, halogen, nitro, trifluoromethyl, and nitrile), heteroaryl where the heteroaryl contains 5 to 6 ring atoms and is optionally $C_{1-4}$ alkyl substituted;

$R_3$ is hydrogen, SEM, $C_{1-5}$alkoxycarbonyl, aryloxycarbonyl, aryl$C_{1-5}$alkyloxycarbonyl, aryl$C_{1-5}$alkyl, substituted aryl$C_{1-5}$alkyl (where the aryl substituents are independently selected from one or more members of the group consisting of $C_{1-5}$alkyl, $C_{1-5}$alkoxy, halogen, amino, $C_{1-5}$alkylamino, and di$C_{1-5}$alkylamino), phthalimido$C_{1-5}$alkyl, amino$C_{1-5}$alkyl, diamino$C_{1-5}$alkyl, succinimido$C_{1-5}$alkyl, $C_{1-5}$alkylcarbonyl, arylcarbonyl, $C_{1-5}$alkylcarbonyl$C_{1-5}$alkyl, aryloxycarbonyl$C_{1-5}$alkyl, heteroaryl$C_{1-5}$alkyl where the heteroaryl contains 5 to 6 ring atoms;

$R_6$ is iodine, chlorine, or bromine; with a compound of Formula IV $$C(C)-(CH_2)_q-X \qquad (IV)$$

where q is 0-9 and

X is hydrogen, $C_{1-5}$alkyl, substituted $C_{1-5}$alkyl, hydroxy, phenyl, substituted phenyl, amino, $C_{1-5}$alkylamino, nitrile, vinyl, ethynyl aryl$C_{1-5}$alkyl, succinimido, phthalimidooxy and halogen.

in the presence of a palladium coupling agent, a suitable solvent, and an organic base under reaction conditions which permit the preparation of a compound of Formula I.

DETAILED DESCRIPTION OF THE INVENTION

The terms used in describing the invention are commonly used and known to those skilled in the art. However, the terms that could have other meanings are defined. The term "FCS" represents fetal calf serum, "TCA" represents trichloroacetic acid and the "RPMI" represents the medium from the Roswell Park Memoria Inst. (Sigma cat # R0833). "Independently" means that when there are more than one substituent, the substitutents may be different. The term "alkyl" refers to straight, cyclic and branched-chain alkyl groups and "alkoxy" refers O-alkyl where alkyl is as defined supra. The term heteroaryl refers to an aromatic ring of five or six members where at least one member is a heteroatom. Suitable heteroatoms include, nitrogen, oxygen and sulfur. In the case of five-membered rings the heteroaryl will contain one sulfur, oxygen, or nitrogen atom and, in addition, may contain up to three additional nitrogens. With six-membered rings the heteroaryl may contain up to three nitrogens. Examples of such heteroaryls include, pyridin-2-yl, pyridin-3-yl, pyridin4-yl, pyrimidin-3-yl, furan-2-yl, furan-3-yl, thiophen-2-yl, thiophen-3-yl, pyridazine, triazine, thiazole, oxazole, pyrazole and the like. "SEM" refers to 2-(trimethylsilyl)ethoxymethyl) and "LDA" refers to lithium diisopropylamide. The symbol "Ph" refers to phenyl, "PHT" refers to phthalimido and the "aryl" includes mono and fused aromatic rings such as phenyl and naphthyl. The symbol C(C) represents an ethylene group:

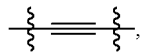

and the symbol $(CH)_2$ represents a vinylene group:

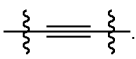

The term "reaction conditions" includes physical parameters such as temperature.

As used in this invention the term "cytokine" refers to the proteins TNF-α and IL-1β. Cytokine related disorders are diseases of humans and other mammals where the overproduction of cytokines causes the symptoms of the disease. The overproduction of the cytokines, TNF-α and IL-1β has been linked to a number of diseases. These cytokine related disorders include but are not limited to rheumatoid arthritis, inflammatory bowel disease, septic shock osteoporosis, osteoarthritis, neuropathic pain, HIV replication, HIV dementia, viral myocarditis, insulin-dependent diabetes, non-insulin dependent diabetes, periodontal disease$_1$ restenosis, alopecia areta, T-cell depletion in HIV infection or AIDS, psoriasis, acute pancreatitis, allograft rejection, allergic inflammation in the lung, atherosclerosis, mutiple sclerosis, cachexia, alzheimer's disease, stroke, Crohn's disease, inflammatory bowel disease, ischemia, congestive heart failure, pulmonary fibrosis, hepatitis, glioblastoma, Guillain-Barre Syndrome, and systemic lupus erythematosus. The term "effective dose" refers to an amount of a compound of Formula I which reduces the amount of TNFα and/or IL-1β which may be detected in a mammal suffering from a cytokine mediated disorder. In addition, the term "effective dose" refers to an amount of a compound of Formula I which reduces the symptoms of a cytokine related disorder.

The compounds of the invention may be prepared by the following schemes, where some schemes produce more than one embodiment of the invention. In those cases, the choice of scheme is a matter of discretion which is within the capabilities of those skilled in the art.

In order to produce the compounds of the invention where A is ethynylene, Scheme I may be used. The starting material for the scheme is a 4,5-disubstituted imidazole of the type 1a. Substituted imidazoles may be prepared following know procedures and the substituents $R_1$ and $R_2$ of the compounds of the invention are determined by the substituents of intermediate 1 a. Intermediate 1a is treated with a base, such as NaH and an inert solvent such as DMF at room temperature for about 30 min to 1 h. Once anion formation is complete, an alkylating agent is added such as phenethyl chloride and the reaction mixture is stirred at about 60–100° C. for about 2–4 h to give intermediates 1b$_1$ and 1b$_2$. These intermediates are separated at this stage to allow for the formation of final products with one predominate isomer. Although the final products may be separated, the separation of 1b$_1$ and 1 b$_2$ leads to higher yields of products. Alternatively intermediates 1b$_1$ and 1b$_2$ can be prepared using the methods described in WO 96/21452, "Certain 1,4,5-Trisubstituted Imidazole Compounds Useful as Cytokine."

Intermediate 1b$_2$ is treated with a strong base such as LDA in an inert solvent such as THF at −78° C. for about 30 min. A source of halogen atoms such as iodine or bromine is added to the formed anion and this mixture is allowed to warm to ambient temperature over 30 min to 1 h to give intermediate 1c where W is iodine. Treatment of 1c with a palladium coupling agent such as bis(acetatato)bis(triphenylphosphine)palladium II, a substituted ethynyl compound, such as 3-butyn-1-ol and an organic base such as triethylamine in an inert solvent such as methylene chloride at reflux gives compounds of the invention of type 1d. Alternatively, 1c may be treated with other palladium coupling agents. The agents must be palladium II entities and include but are not limited to bis(triphenylphosphine)palladiumdichloride, bis(acetonitrile)chloronitropalladium (II), bis(acetonitrile)-dichloronitropalladium (II), and bis(benzonitrile)dichloropalladium (II). In addition catalytic amounts of copper catalysts, such as copper iodide may be added to increase the speed of the reaction and/or reduce the reaction temperature from reflux to room temperature.

Although Scheme 1 is used to prepare a compound of the invention where A is ethynylene, n is 1, q is 2, X is hydroxy, $R_1$ is 1,3-pyrimidin4-yl, $R_2$ is 4-chlorophenyl and $R_3$ is phenethyl, the scheme may be used to prepare other products. For example, to vary $R_3$, the alkylating agent, may be replaced by either another alkylating agent or an acylating agent. To prepare compounds where $R_3$ is $C_{1-5}$alkoxycarbonyl, aryloxycarbonyl, aryl$C_{1-5}$alkoxycarbonyl, $C_{1-5}$alkylcarbonyl, and arylcarbonyl, an acylating agent replaces the benzyl chloride in Scheme 1. For example, to prepare compounds where $R_3$ is benzoyl, benzoyl chloride relaces benzyl chloride. If compounds where $R_3$ is substituted aryl$C_{1-5}$alkyl, amino$C_{1-5}$alkyl, substituted amino$C_{1-5}$alkyl and $C_{1-5}$alkyl are desired, benzyl chloride may be replaced with any number of alkylating agents. For example, to prepare compounds where $R_3$ is a substituted amino$C_{1-5}$alkyl, 1-bromo-3-dimethylaminopropane may be used is place of phenethyl chloride.

In order to vary X and q, a variety of known substituted ethynylene compounds may be used. For example if one replaces 3-butyn-1-ol with propargyl chloride, compounds where q is 1 and X is Cl, may be produced. Compounds where q is 0–9 and X is $C_{1-5}$alkyl, substituted $C_{1-5}$alkyl, phenyl, substituted phenyl, amino, $C_{1-5}$alkylamino, nitrile, vinyl, ethynyl aryl$C_{1-5}$-alkyl, succinimido, phthalimidooxy and halogen may all be prepared in this manner.

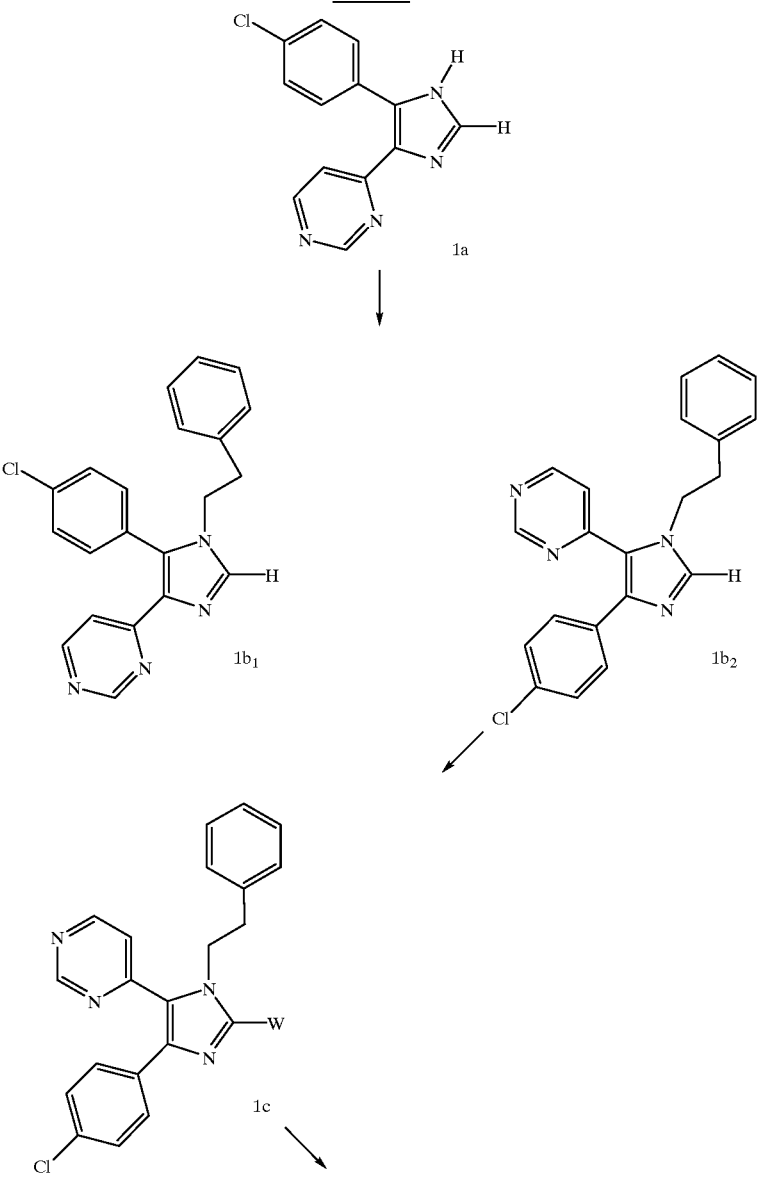

Scheme 1

-continued

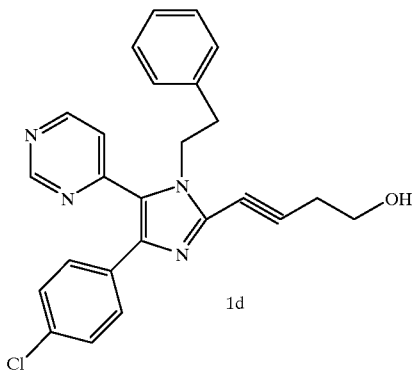

1d

Scheme 2 may be used to prepare compounds of the invention where A is vinylene. Intermediate 1a is the starting material for this scheme and is treated with a base such as NaH and an inert solvent such as DMF at room temperature for about 30 min to 1 h. Once anion formation is complete, 2-(trimethylsilyl)ethoxymethylchloride is added at room temperature and stirred for about 3–5 h to give intermediates $2a_1$ and $2a_2$. As in Scheme 1, the isomers are separated at this stage. Intermediate $2a_2$ is treated with a strong base such as n-butyllithium in an inert solvent such as THF at −78° C. for about 1 h. A halogen source such as iodine is added and the mixture is stirred at ambient temperature for about 1 h to give intermediate 2b. Treatment of 2b with a palladium coupling agent such as bis(acetatato)bis(triphenylphosphine)palladium II, trimethylsilylacetylene and triethylamine at about 70° C. for 18 to 24 h gives ethnyl intermediate 2c. This intermediate is treated with aqueous HBr in an alcoholic solvent such as EtOH at reflux for about 3–6 h to give a compound of Formula 1 where A is vinyl and X is Br.

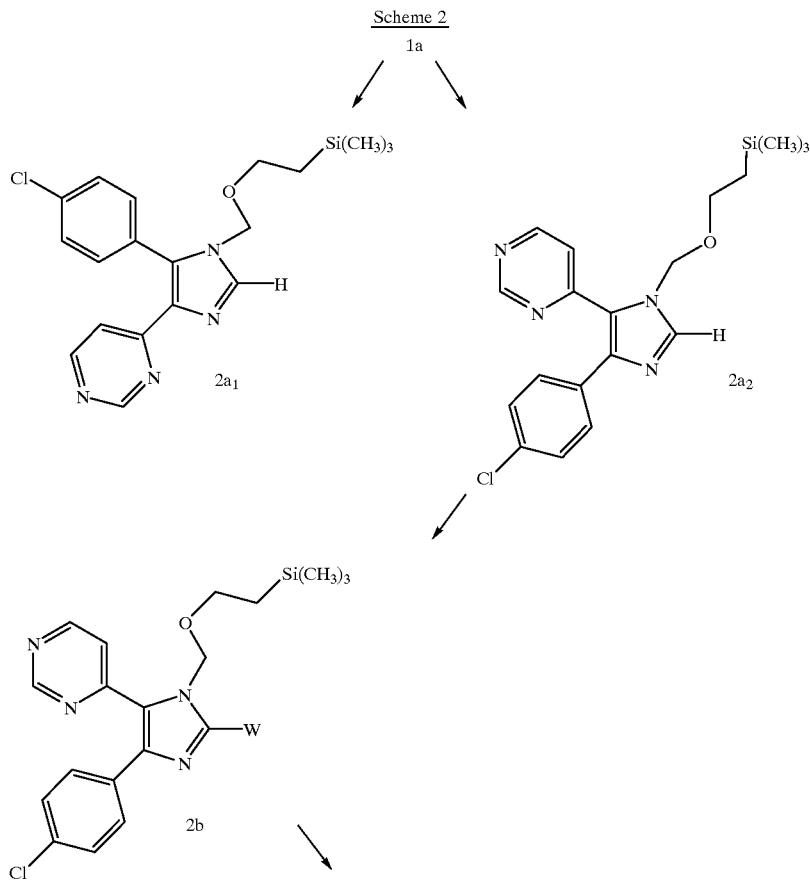

Scheme 2

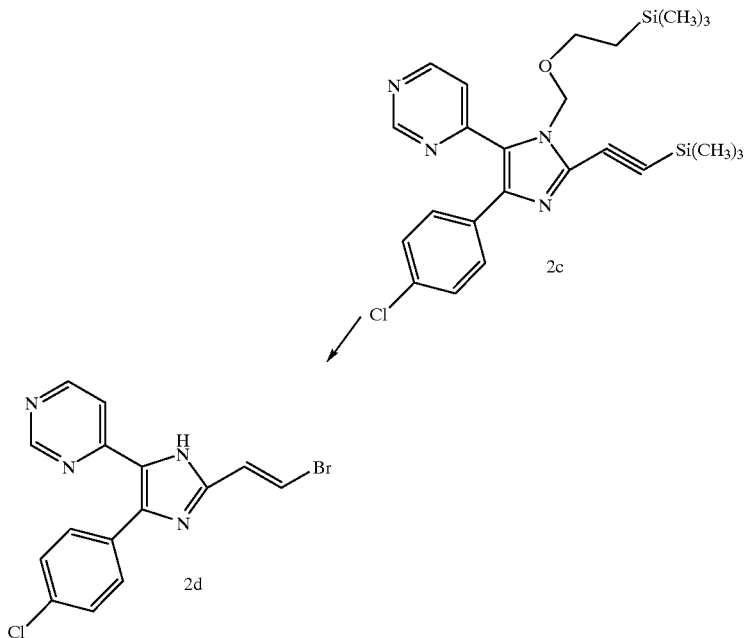

Another method of preparing compounds where A is vinylene, is illustrated by Scheme 3. The starting point for this scheme is the treatment of intermediate $2a_2$ with a base such as n-BuLi in an inert solvent such as THF at about −78° C. under an inert atmosphere for about 15–30 min. DMF is added and this mixture is stirred at ambient temperature for about 1–5 h to give the aldehyde intermediate 3a. Treatment of 3a with Wittig reagent formed from triphenylphosphine and carbon tetrabromide, triethylamine and an inert solvent such as methylene chloride gives the vinyl compound 3b. This compound may be treated with an aqueous acid such as HCl at about room temperature over several hours to give the 2-substituted derivative 3c.

Due to the variety of known Wittig reagents, many of the compounds of the invention where A is vinyl may be prepared by Scheme 3. For example, to produce the compounds of the invention where A is vinylene, q is 1 and X is vinyl, the Wittig reagent prepared from triphenylphosphine and allyl bromide replaces the Wittig reagent used in Scheme III. Compounds where q is 1–9 and X is ethynyl, vinyl, substituted vinyl, $C_{1-5}$alkyl, substituted $C_{1-5}$alkyl, cycloalkyl, phenyl, ara$C_{1-5}$alkyl, $C_{1-5}$alkylamino and nitrile may be prepared by this scheme.

In addition to compounds where A is vinylene, Scheme 3 may be used to produce compounds where A is ethynylene and X is hydroxy substituted arylalkyl. Treatment of 3c with a base such as n-BuLi in an inert solvent such as THF at −78° C., followed by treatment with benzaldehyde gives the desired product 3d.

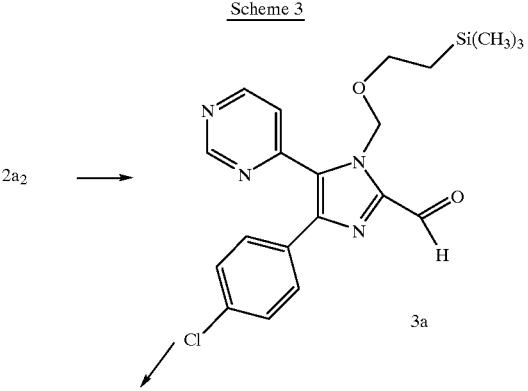

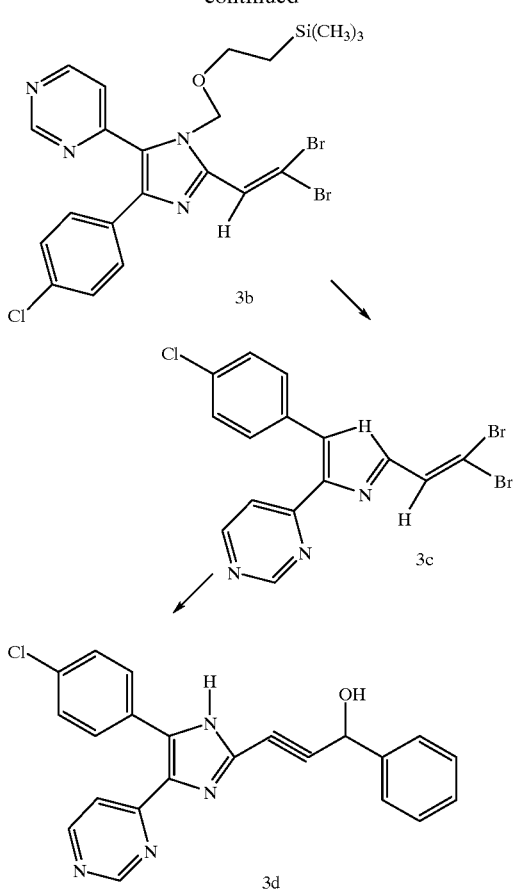

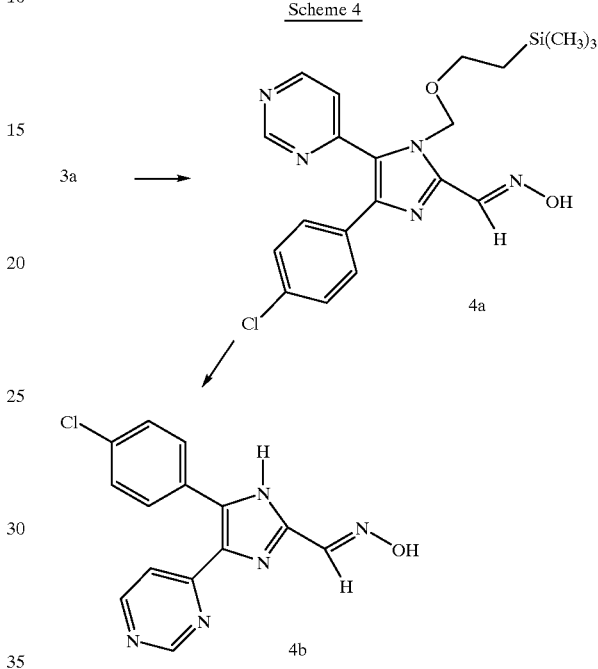

intermediate 4a. The SEM group of 4a may be removed by treatment with an aqueous acid and an alcoholic solvent at reflux for about 4 h to give the desired product 4b. In order to produce the compounds of the invention where $R_5$ is $C_{1-5}$alkyl, phenyl, phenyl$C_{1-5}$alkyl, hydroxylamine may be replaced with the known corresponding O-substituted hydroxylamines such as O-benzylhydroxylamine.

To produce the compounds of the invention where A is

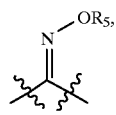

when $R_5$ is hydrogen, Scheme 4 may be used. Treatment of intermediate 3a with hydroxylamine in an inert solvent such as MeOH for about 3–6 h at room temperature gives The compounds of the invention where X is $C_{1-5}$alkylthio, substituted $C_{1-5}$alkylthio, $C_{1-5}$alkylsulfonyl, phenylsulfonyl and substituted phenylsulfonyl may be produced by Scheme 5. Treatment of 1c with 5-chloro-1-pentyne and a palladium coupling agent as previously described gives compound 5a. Displacement of the chloride with nucleophilic agents such as 2-mercaptoethanol in an inert solvent such as acetonitrile at room temperature gives the thiol 5b. Treatment of 5b with aqueous oxone and an inert solvent such as MeOH at ambient temperature over 3–6 h gives the sulfone compound 5c.

Scheme 5

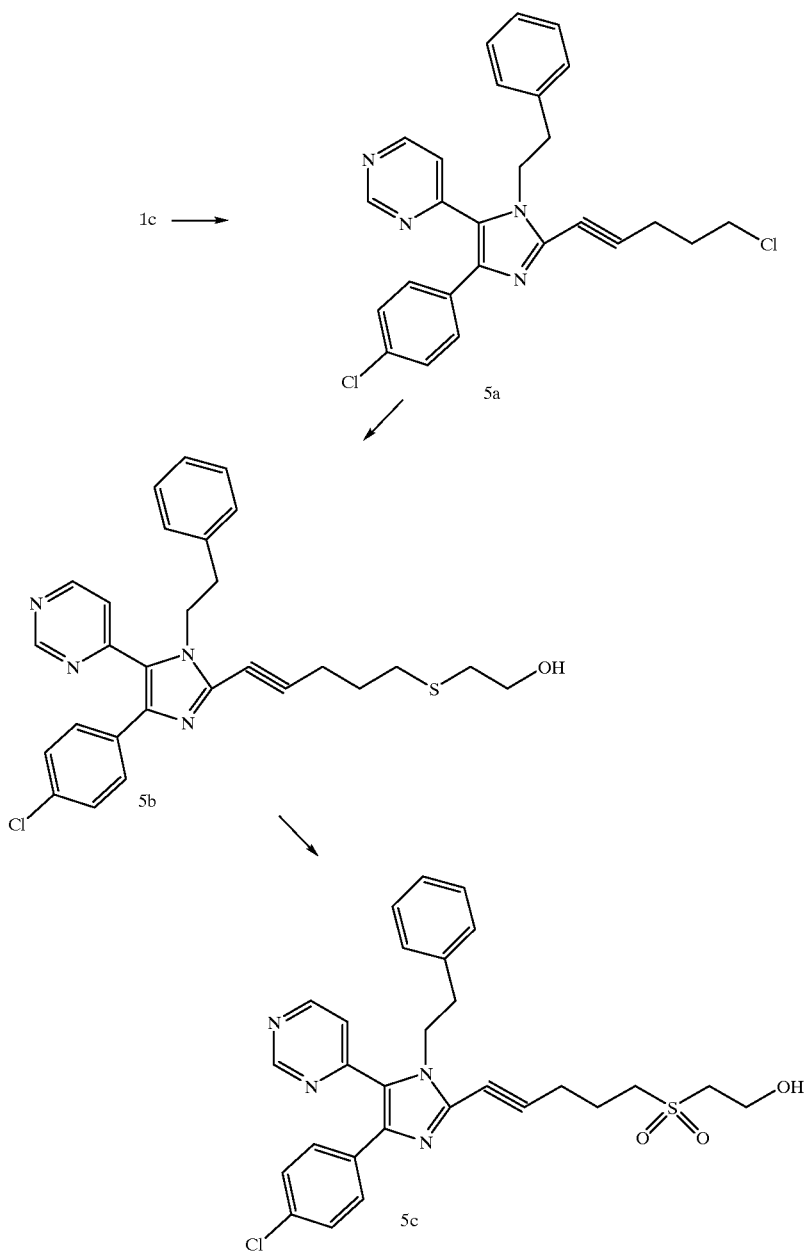

To produce compounds of the invention where X is $C_{1-5}$alkoxycarbonyloxy, compound 1d may be used as illustrated by Scheme 6. Treatment of compound 1d with an acylating agent such as methyl chloroformate at room temperature in an inert solvent and a mild base gives compound 6a. This method may be used to produce compounds of the invention where X is $C_{1-5}$alkylcarbonyloxy, phenylcarbonyloxy, phenyl$C_{1-5}$alkylcarbonyloxy, aminocarbonyloxy, $C_{1-5}$alkylaminocarbonyloxy, di $C_{1-5}$alkylaminocarbonyloxy, $C_{1-5}$alkoxycarbonyloxy, substituted $C_{1-5}$alkoxycarbonyloxy, phenoxycarbonyloxy and substituted phenoxycarbonyloxy by replacing methyl chloroformate with known acylating agents. For example to prepare compounds where X is methylaminocarbonyloxy, replace methyl chloroformate with methyl isocyanate.

The compounds where X is halogen may be synthesized using 1d as illustrated by Scheme 6. Treatment of compound 1d with triphenylphosphine and a halogen source such as carbon tetrachloride at room temperature gives compound 6b. Treatment of 6b at room temperature with a nucleophilic agent such as diethyl amine gives compound 6c.

Scheme 6
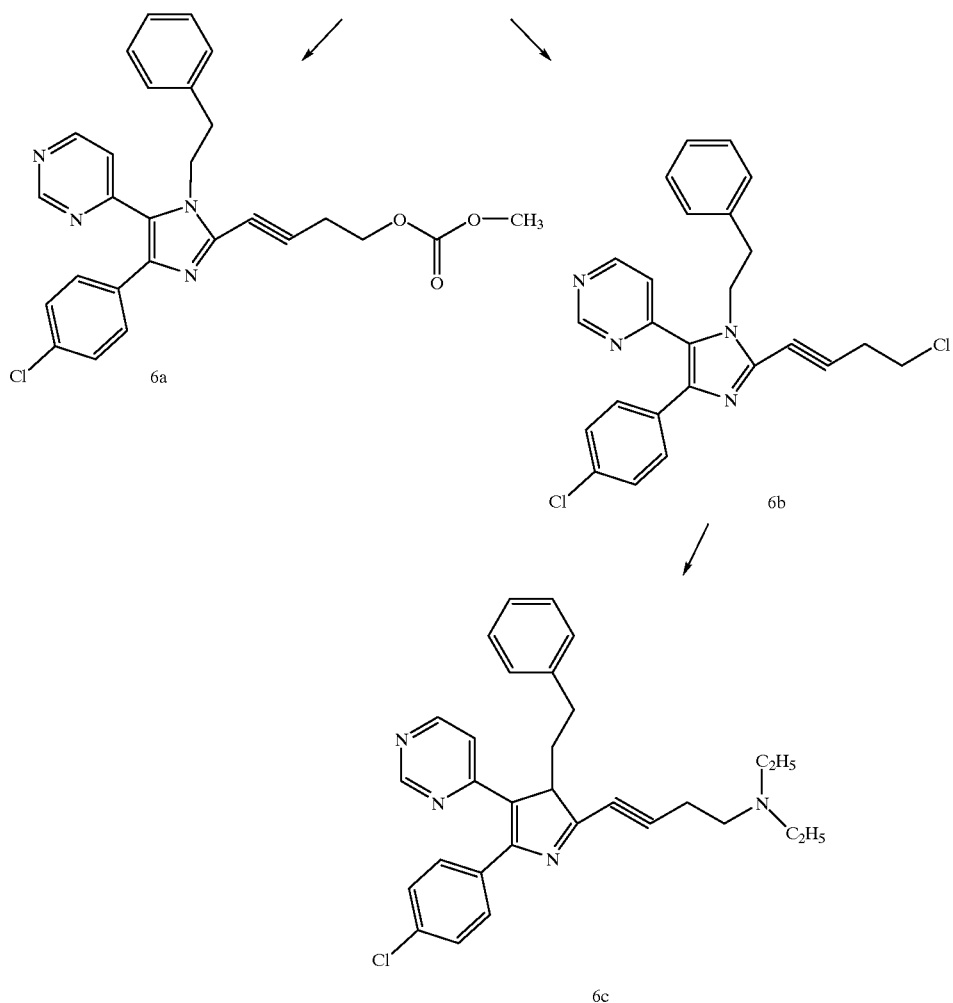
Although the claimed compounds are useful as inhibitors of TNF-α and IL-1β some compounds are more active than others and are either preferred or particularly preferred.
The preferred compounds of Formula I include:
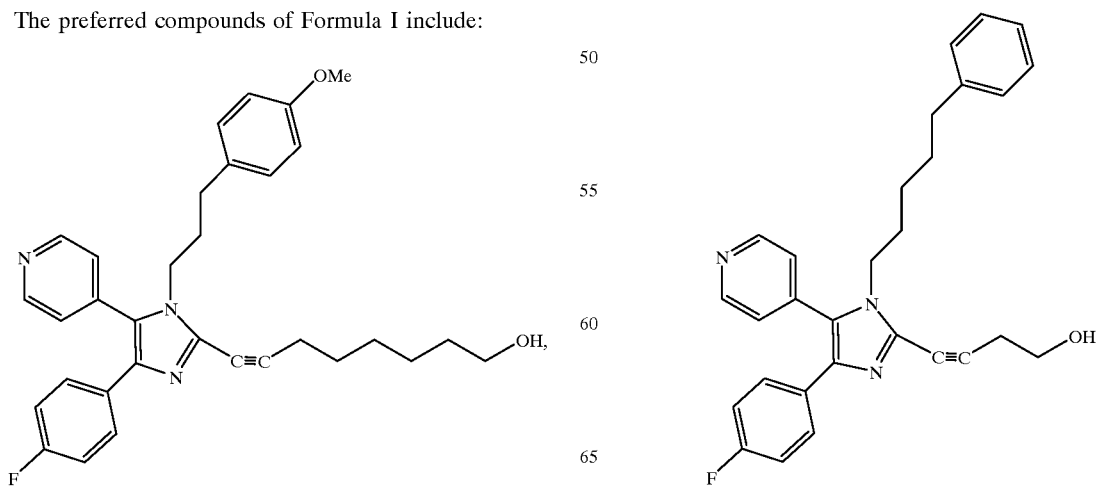

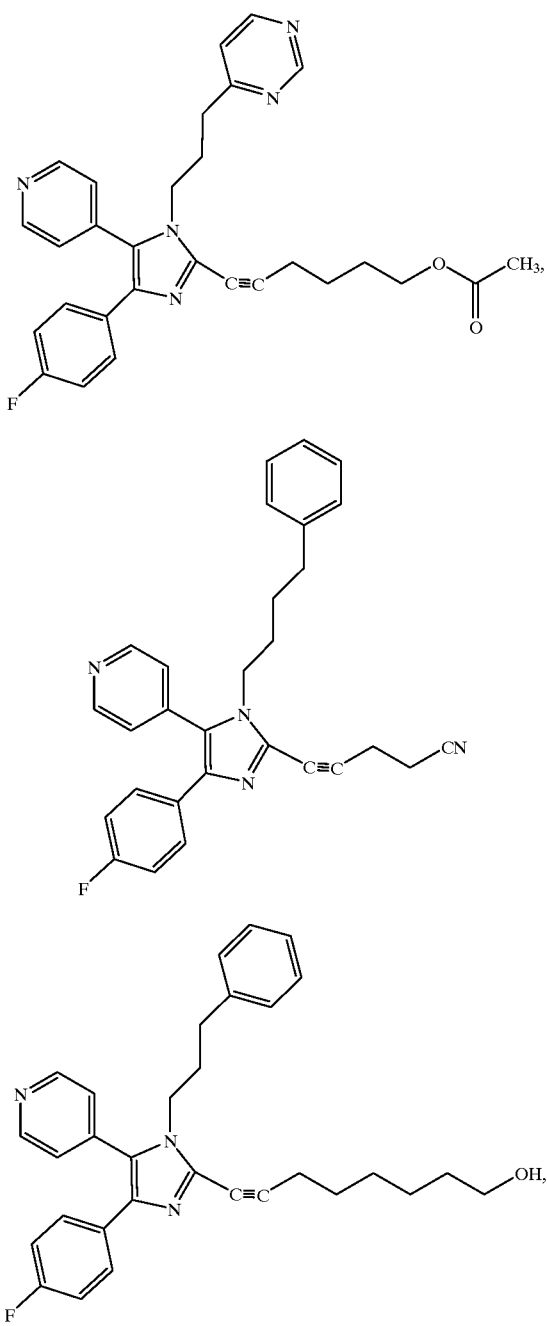
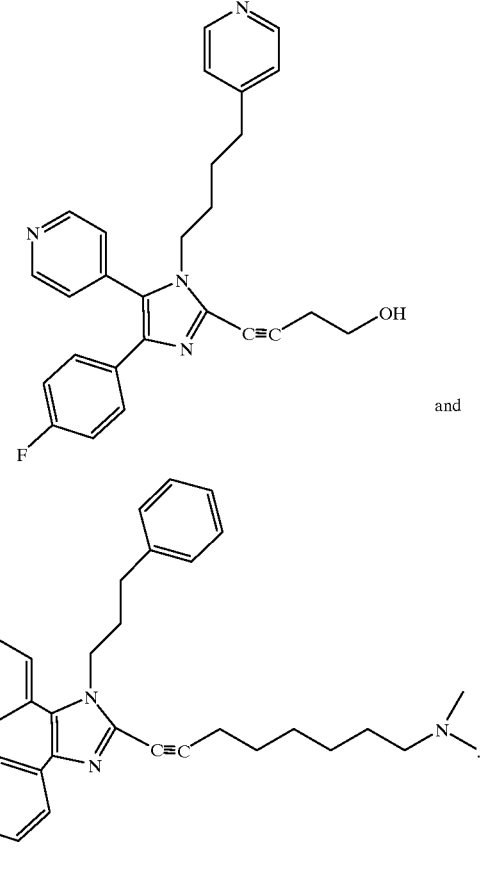

The particularly preferred "R₁"s are phenyl or substituted phenyl where the phenyl substituents are halogen or nitrile.

The particularly preferred "R₂"s are pyrid4-yl, pyrimidin4-yl and 2-butyl-pyridin4-yl.

The particularly preferred "R₃"s are hydrogen, (CH₂)₃Ph and (CH₂)₃PHT.

The particularly preferred "A"s are vinylene and ethynylene.

The particularly preferred "q"s are 0–6.

The particularly preferred "X"s are hydrogen, hydroxyl, chlorine, nitrile, cyclopentyl, $C_{1-5}$alkylcarbonyloxy, phenylcarbonyloxy, phenyl$C_{1-5}$alkylcarbonyloxy, aminocarbonyloxy, $C_{1-5}$alkylaminocarbonyloxy and di$C_{1-5}$alkylaminocarbonyloxy.

Compounds of Formula I may be used in pharmaceutical compositions to treat patients (humans and other primates) with disorders related to the overproduction of inflammatory cytokines, particularly TNF-α. The preferred route is oral administration, however compounds may be administered by intravenous infusion or topical administration. Oral doses range from about 0.05 to 100 mg/kg, daily. Some compounds of the invention may be orally dosed in the range of about 0.05 to about 50 mg/kg daily, while others may be dosed at 0.05 to about 20 mg/kg daily. Infusion doses can range from about 1.0 to $1.0 \times 10^4$ $\mu$g/kg/min of inhibitor, admixed with a pharmaceutical carrier over a period ranging from several minutes to several days. For topical administration compounds of Formula I may be mixed with a pharmaceutical carrier at a concentration of about 0.1 to about 10% of drug to vehicle.

The pharmaceutical compositions can be prepared using conventional pharmaceutical excipients and compounding techniques. Oral dosage forms may be elixers, syrups, capsules tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated and used as free bases, however the compounds may be isolated and used as their pharmaceutically acceptable salts. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexane-sulfamic and saccharic.

BIOLOGICAL EXAMPLES

The biological activity of the compounds of the invention was demonstrated by in vitro and in vivo assays. As discussed previously, agents which inhibit the activity of the enzyme p38, inhibit the production of the inflammatory cytokines TNF-$\alpha$, and IL-1$\beta$. Compounds of the invention were measured for their ability to inhibit the activity of p38 by the following in vitro assay.

A solution (38 $\mu$L) of purified recombinant p38 (where the amount of enzyme was determined empirically considering the linear range of the assay and the acceptable signal to noise ratio; 6xHis-p38 expressed in $E.coli$), myelin basic protein substrate (also determined empirically), a buffer of pH 7.5 (Hepes:25 mM, $MgCl_2$: 10 mM, $MnCl_2$: 10 mM) were added to 92 wells of a 96-well round bottom polypropylene plate. The remaining wells were used for control ("CTRL") and background ("BKG"). The CTRL was prepared with the enzyme, substrate buffer and 2% DMSO, and the BKG was prepared with substrate buffer and 2% DMSO. A solution (12 $\mu$L) of the test compound in DMSO (compounds were diluted to 125 $\mu$M in 10% DMSO/$H_2O$ and assayed at 25 $\mu$M where the final DMSO concentration was 2%) was added to the testing wells. The ATP/$^{33}$P-ATP solution (10 $\mu$L: containing 50 $\mu$M unlabeled ATP and 1 $\mu$Ci $^{33}$P-ATP) was added to all wells and the completed plates were mixed and incubated at 30° C. for 30 min. Ice-cold 50% TCA10 mM sodium phosphate (60 $\mu$L) were added to each well and the plates were kept on ice for 15 min. The contents of each well were transferred to the wells of a 96-well filterplate (Millipore, MultiScreen-DP) and the filterplate was placed on a vacuum manifold, fitted with a waste collection tray. The wells were washed five times with 10% TCA/10 mM sodium phosphate (200 $\mu$L) under vacuum. MicroScint-20 scintillant was added, the plates were sealed using Topseal-S sheets and counted in a Packard TopCount scintillation counter using a $^{33}$P liquid program with color quench correction, where the output is in color quench-corrected cpm. The % inhibition of the test compounds was calculated by the following formula: % inhibition=[1−(sample−BKG)/(CTRL−BKG)]×100.

Although compounds were initially tested at 20 $\mu$M, if warranted the compounds were tested at 4-fold increments above and below that concentration. In addition, $IC_{50}$s were calculated for some compounds using the Deltagraph 4-parameter curve fitting program.

Aside from the enzyme assay, many of the compounds of the invention were tested in an in vitro whole cell assay using peripheral blood mononuclear cells ("PBMC") which were obtained from human blood as follows. Freshly obtained venous blood was anticoagulated with heparin, diluted with an equal volume of phosphate buffered saline ("PBS") and placed in a sterile tube or other container. Aliquots (30 mL) of this mixture were transferred to centrifuge tubes which were underlaid with Ficoll-Hypaque (15 mL). The prepared tubes were centrifuged at 400×g without braking for 30 min at room temperature. Approximately ½ to ⅔ of the platelet layer above the mononuclear cell band was removed with a pipette. The majority of the mononuclear cell layer was carefully removed using a pipette and these PBMCs were diluted with PBS and spun at 600×g for 15 min. The resulting PBMCs were washed with another portion of PBS and spun at 400×g for 10 min at room temperature. The recovered pellets were diluted in low endotoxin RPMI / 1% FCS culture medium and gave a cell concentration of $0.5-2.0 \times 10^6$ PMBC/ mL. A small volume of the suspension was removed for counting on a hemocytometer and the remaining preparation was centrifuged at 200×g for 15 min at room temperature. The recovered pelleted PMBC were resuspended in RPMI /1% FCS to a concentration of $1.67 \times 10^6$/mL.

To run the assay, the PBMC suspension (180 $\mu$L) was transferred to duplicate wells of a 96-well flat-bottom microtiter plate and incubated for 1 h at 37° C. A solution of test compound (10 $\mu$L: prepared at 20×the desired final concentration) was added to each well and the plate was incubated for 1 h at 37° C. A solution (10 $\mu$L) of LPS in RPMI /1% FCS (200 ng/mL) was added and the wells were incubated overnight at 37° C. The supernate (100 $\mu$L) was removed from each well and diluted with RPMI / 1% FCS (400 $\mu$L). The samples were analyzed for TNF-$\alpha$ using a commercial ELISA kit (Genzyme).

The IL-1$\beta$ activity of select compounds of the invention was determined by the following in vitro assay. Plastic-adherent cells were prepared from PBMC. Briefly, PBMCs were added to the wells of a 96-well plate as above, incubated for 1 h at 37° C., and the adherent cells prepared by gently resuspending the non-adherent cells with a pipettor, removing and discarding them and gently washing the wells 3 times with 200 $\mu$L culture medium. Additional culture medium (180 $\mu$L) was added to the wells after the final wash. Compound addition, LPS stimulation, incubation and supernate harvest were as for TNF-$\alpha$. Supernates were assayed for interleukin-1$\beta$ using a commercial ELISA (Genzyme).

Compounds 4 and 36 inhibited the production of IL-1$\beta$ at $IC_{50}$s of 7 and 13 nM respectively.

The ability of the compounds of Formula I to inhibit LPS induced TNF-$\alpha$ production was demonstrated in the following in vivo rodent assays. Mice (BALB / cJ females, Jackson Laboratories) or rats (Lewis males, Charles River) were fasted for 30 min prior to oral dosing with 5–10 mL/Kg of test compound at 5–50 mg/kg. Thirty minutes after dosing, the animals were injected intraperitoneally with LPS at 1 mg/kg and returned to their cages for 1 h. Animals were anesthetized by $CO_2$, exsanguinated by cardiac puncture and whole blood collected (0.1–0.7 mL). The blood was allowed to clot and serum was transferred to a centrifuge tube. This sample was centrifuged, serum was collected, aliquoted and frozen at −80° C. Samples were tested by commercial ELISAs for TNF-α (Endogen for mouse TNF-α and Biosource for rat TNF-α).

In addition to their in vivo TNF-α activity, a compound of Formula I inhibits polyarthritis in an in vivo rat model as follows. On day 0, male Lewis rats were injected subcutaneously near the base of the tail with 100 μl of a 7.5 mg/ml suspension of heat-killed Mycobacterium butyricum in mineral oil. Groups of rats were dosed orally, once per day, from day 0 through the end of the experiment with HCl as a negative control, or with 20 or 50 mg/kg of Cpd. 4. As a positive control for inhibition, one group was dosed with HCl on days 0–9, and then with 20 mg/kg (or 50 mg/kg)of cyclosporine (Cys) from day 10 through the end of the experiment. Under these conditions, the animals' paws in the negative control group begin to swell on days 11–12. The paw volumes of both rear paws were determined on a mercury plesthysmograph on days 8–10, depending on the experiment, and again on days 14, 17, and either 19 or 21. The data were analyzed as the increase in paw volumes compared to the day 8–10 baseline measurements. The data obtained in four experiments is listed in Table A.

TABLE A

| Expt. # | Dose (mg/kg) | Ave. % decrease in paw swelling |
|---|---|---|
| 1 | 20 | 79 |
| 2 | 20 | 4 |
| 3 | 50 | 71 |
| 4 | 50 | 20 |

Select compounds of the invention are listed in Table B. Most compounds were tested for their ability to inhibit p38 and TNF-α, however some compounds were screened in one assay. The $IC_{50s}$ are listed for the majority of compounds and if this calculation is unavailable, the % inhibition is listed for a given concentration. In addition to the biological data, the synthetic schemes used to prepare the compounds are listed. Since imidazoles which are unsubstituted at the 1-position are subject to tautomerization, the substituents listed for $R_1$ and $R_2$ are interchangeable when $R_3$ is hydrogen.

TABLE B

| Cpd. | $R_1$ | $R_2$ | $R_3$ | $R_4$ | p-38 $IC_{50}$ μm | TNF-α $IC_{50}$ nm | Scheme |
|---|---|---|---|---|---|---|---|
| 4 | 4-F—Ph | 4-pyr | $(CH_2)_3Ph$ | $C(C)(CH_2)_2OH$ | 0.65 | 3.0 | 1 |
| 8 | 4-F—Ph | 4-pyr | H | $(CH)_2Cl$ | 1.5 | | 2 |
| 10 | 4-pyr | 4-F—Ph | SEM | $(CH)_2Br_2$ | 16% @ 5 μm | | 3 |
| 11 | 4-F—Ph | 4-pyr | H | $C(C)CH(OH)$-Ph | | 400 | 3 |
| 13 | 4-F—Ph | 4-pyr | H | $CH(N)OH$ | | 45 | 4 |
| 14 | 4-F—Ph | 4-pyr | $(CH_2)_3Ph$ | $C(C)(CH_2)_3Cl$ | | 4 | 6 |
| 15 | 4-F—Ph | 4-pyr | $(CH_2)_3Ph$ | $C(C)(CH_2)_2$—$OC(O)NHPh$ | | 38 | 6 |
| 16 | 4-F—Ph | 4-pyr | $(CH_2)_3Ph$ | $C(C)(CH_2)_2Cl$ | | 6 | 6 |
| 17 | 4-F—Ph | 4-pyr | $(CH_2)_3Ph$ | $C(C)(CH_2)_2N(CH_3)_2$ | | 3 | |
| 18 | 4-F—Ph | 4-pyr | SEM | $(CH)_2Br_2$ | | 1500 | 3 |
| 19 | 4-F—Ph | 4-pyr | H | $C(C)(CH_2)_3OH$ | | 85 | 1 |
| 20 | 4-pyr | 4-F—Ph | SEM | $C(C)(CH_2)_2OH$ | | >10,000 | 1 |
| 21 | 4-F—Ph | 4-pyr | H | $C(C)(CH_2)_2OH$ | | 80 | 1 |
| 22 | 4-F—Ph | 4-pyr | H | $C(C)(CH_2)_3PHT$ | | 700 | 6 |
| 23 | 4-pyr | 4-F—Ph | SEM | $C(C)(CH_2)_4OH$ | | >2,000 | 1 |
| 24 | 4-F—Ph | 4-pyr | H | $C(C)(CH_2)_4OH$ | | 100 | 1 |
| 25 | 4-pyr | 4-F—Ph | SEM | $C(C)(CH_2)_3CN$ | | >2,000 | 1 |
| 26 | 4-pyr | 4-F—Ph | SEM | $C(C)(CH_2)_2CH_3$ | | >2,000 | 1 |
| 27 | 4-pyr | 4-F—Ph | H | $C(C)(CH_2)_3CN$ | | 55 | 1 |
| 28 | 4-pyr | 4-F—Ph | H | $C(C)(CH_2)_2CH_3$ | | 80 | 1 |
| 29 | 4-pyr | 4-F—Ph | H | $C(C)(CH_2)_3PHT$ | | 200 | 1 |
| 30 | 4-F—Ph | 4-pyr | H | $C(C)H$ | | 150 | 6 |
| 31 | 4-F—Ph | 4-pyr | H | $C(C)Br$ | | 250 | 1 |
| 32 | 4-F—Ph | 4-pyr | H | $CH(N)OCH_2Ph$ | | 80 | 2 |
| 33 | 4-F—Ph | 4-pyr | H | $CH(N)O$—$CH_2(4\text{-}NO_2Ph)$ | | 150 | 4 |
| 34 | 4-F—Ph | 4-pyr | $(CH_2)_3Ph$ | $C(C)(CH_2)_2CH_3$ | | 10.0 | 1 |
| 35 | 4-F—Ph | 4-pyr | $(CH_2)_3Ph$ | $C(C)(CH_2)_3OH$ | 99% @ 20 μm | 8.0 | 1 |
| 36 | 4-F—Ph | 4-pyr | $(CH_2)_3Ph$ | $C(C)(CH_2)_3CN$ | 1.5 | 9.0 | 1 |
| 37 | 4-F—Ph | 4-pyr | $(CH_2)_3PHT$ | $C(C)(CH_2)_2OH$ | | 160 | 1 |
| 38 | 4-F—Ph | 4-pyr | $(CH_2)_3Ph$ | $C(C)(CH_2)_3Ph$ | | 40 | 1 |
| 39 | 4-F—Ph | 4-pyr | $(CH_2)_3Ph$ | $C(C)(CH_2)_3S(CH_2)_3CH_3$ | | 200 | 5 |
| 40 | 4-F—Ph | 4-pyr | $(CH_2)_3Ph$ | $C(C)(CH_2)_3$—$SO_2(CH_2)_3CH_3$ | | 6.5 | 5 |
| 41 | 4-F—Ph | 4-pyr | $(CH_2)_3Ph$ | $C(C)CH_2cyclopentyl$ | | 28 | 1 |
| 42 | 4-F—Ph | 4-pyr | $(CH_2)_3Ph$ | $C(C)(CH_2)_5CH_3$ | | 90 | 1 |
| 43 | 4-F—Ph | 4-pyr | $(CH_2)_3Ph$ | $C(C)(CH_2)_4OH$ | 98% @ 20 μm | 5.2 | 1 |

TABLE B-continued

![structure: imidazole with R1, R2, R3, R4 substituents]

| Cpd. | R₁ | R₂ | R₃ | R₄ | p-38 IC$_{50}$ μm | TNF-α IC$_{50}$ nm | Scheme |
|---|---|---|---|---|---|---|---|
| 44 | 4-F—Ph | 4-pyr | H | (CH)$_2$Br$_2$ | 93% @ 20 μm | 200 | 2 |
| 45 | 4-F—Ph | 4-pyr | SEM | C(C)(CH$_2$)$_3$—<br>—N-Succinimide | | 650 | 1 |
| 46 | 4-F—Ph | 4-pyr | H | (CH)$_2$CN | | 250 | 1 |
| 47 | 4-F—Ph | 4-pyr | (CH$_2$)$_3$Ph | C(C)CH$_2$OH | | 7.2 | 1 |
| 48 | 4-F—Ph | 4-pyr | (CH$_2$)$_3$Ph | C(C)CH$_2$OPHT | | 85 | 1 |
| 49 | 4-F—Ph | 4-pyr | (CH$_2$)$_3$Ph | C(C)(CH$_2$)$_2$OCH$_3$ | | 3 | 6 |
| 50 | 4-F—Ph | 4-pyr | (CH$_2$)$_3$Ph | C(C)(CH$_2$)$_2$OCOPh | | 2 | 6 |
| 51 | 4-F—Ph | 4-pyr | (CH$_2$)$_3$Ph | C(C)(CH)$_2$H | | 5.5 | 1 |
| 52 | 4-F—Ph | 4-pyr | (CH$_2$)$_3$Ph | C(C)(CH$_2$)$_2$OCOCH$_3$ | | 2.6 | 6 |

The in vivo test results for select compounds of the invention are listed in Table C. The compounds were tested for their abity to inhibit TNF-α production in mice and/or rats and the data is listed as % inhibition at 25 mg/kg.

TABLE C

![structure: imidazole with R1, R2, R3, R4 substituents]

| | | | | | % Inhibition TNF-α | |
|---|---|---|---|---|---|---|
| Cpd. | R₁ | R₂ | R₃ | R₄ | Mice | Rats |
| 4 | 4-F—Ph | 4-pyr | (CH$_2$)$_3$Ph | C(C)(CH$_2$)$_2$OH | 49.6 | 91 |
| 19 | 4-F—Ph | 4-pyr | H | C(C)(CH$_2$)$_3$OH | 29 | |
| 24 | 4-F—Ph | 4-pyr | H | C(C)(CH$_2$)$_4$OH | 73 | |
| 26 | 4-pyr | 4-F—Ph | SEM | C(C)(CH$_2$)$_2$CH$_3$ | 0 | |
| 27 | 4-pyr | 4-F—Ph | H | C(C)(CH$_2$)$_3$CN | 95 | |
| 28 | 4-pyr | 4-F—Ph | H | C(C)(CH$_2$)$_2$CH$_3$ | 88 | |
| 34 | 4-F—Ph | 4-pyr | (CH$_2$)$_3$Ph | C(C)(CH$_2$)$_2$CH$_3$ | 53 | |
| 35 | 4-F—Ph | 4-pyr | (CH$_2$)$_3$Ph | C(C)(CH$_2$)$_3$OH | 68 | |
| 36 | 4-F—Ph | 4-pyr | (CH$_2$)$_3$Ph | C(C)(CH$_2$)$_3$CN | 69.3 | |
| 43 | 4-F—Ph | 4-pyr | (CH$_2$)$_3$Ph | C(C)(CH$_2$)$_4$OH | 53 | |

PREPARATIVE EXAMPLES

In order to illustrate the invention the following examples are included. These examples do not limit the invention. They are only meant to suggest a method of practicing the invention. Those skilled in the art may find other methods of practicing the invention, which are obvious to them. However those methods are deemed to be within the scope of this invention.

EXAMPLE 1

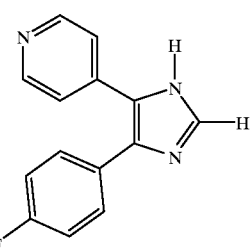

5(4)-(4-Fluorophenyl)-4(5)-(4-pyridyl)imidazole
Cpd. 1

A solution of selenium dioxide (4.82 g, 43.4 mmol) in H$_2$O (20 mL) was added to a solution of 1-(4-fluorophenyl)-

2-(4-pyridyl)-2-ethanone (9.33 g, 43.4 mmol) in dioxane (100 mL) and the resulting mixture was heated at reflux for 2 h. This mixture was concentrated in vacuo, triturated with ethyl acetate and filtered. The residue was purified by column chromatography using ethyl acetate/hexane (1:1) as an eluent to give 1-(4-fluorophenyl)-2-(4-pyridyl)-1,2-ethandione. A mixture of ammonium acetate (25.25 g, 0.328 mol) and hexamethylenetetraamine (9.18 g, 65.5 mmol) was added to a solution of the isolated dione dissolved in acetic acid (150 mL). This mixture was stirred at 80° C. for 2 h, poured into concentrated ammonium hydroxide (200 mL) and the resulting precipitate was filtered, washed with H₂O and dried to give the title compound as a solid: mp 242–44.3° C.; MS 240 (MH⁺).

EXAMPLE 2

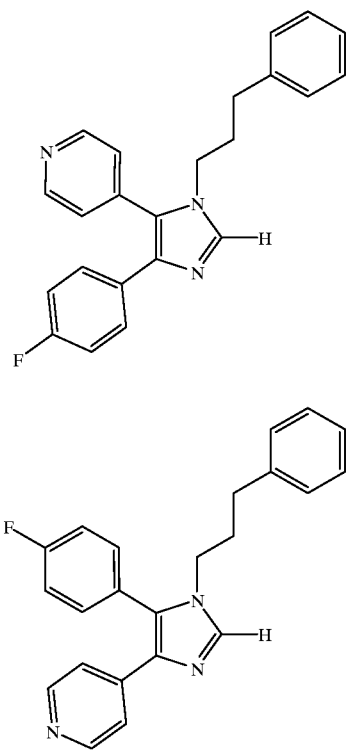

2a

2b 4-(4-Fluorophenyl)-1-(3-phenylpropyl)-5-(4-pyridyl)imidazole

Cpd. 2a 5-(4-Fluorophenyl)-1-(3-phenylpropyl)4-(4-pyridyl)imidazole

Cpd. 2b

60% Sodium hydride (1.32 g, 33 mmol) was added to a mixture of compound 1 (7.15 g, 29.9 mmol) in DMF (70 mL) and stirred for 30 min. 3-Bromophenylpropane ((5.05 mL, 33 mmol) was added and the reaction mixture was stirred under N₂ at 60° C. for 2 h. The mixture was poured into H₂O and extracted with several portions of ethyl acetate. The combined organic layer was washed with H₂O, concentrated in vacuo and purified by column chromotography on silica gel using ethyl acetate as an eluent. Compound 2a is the more polar compound and was isolated as a solid: mp 70–74° C.; MS 358 (MH⁺). Compound 2b was the least polar compound and was isolated as a solid: mp 107.5–112.5 ° C.

EXAMPLE 3

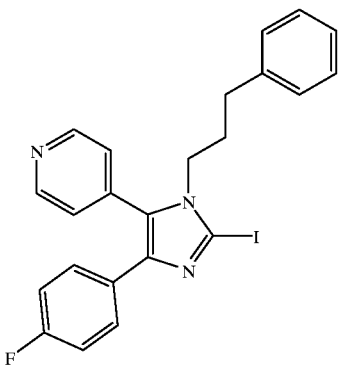

4-(4-Fluorophenyl)-2-iodo-1-(3-phenylpropyl)-5-(4-pyridyl)imidazole

Cpd. 3

2M Lithium diisopropylamide/THF (17 mL) was added to a solution of compound 2a (9.69 g, 27.1 mmol) at −78° C. and this mixture was stirred at −78° C. for 15 minutes. Iodine (10.0 g, 39.4 mmol) was added and the resulting mixture was allowed to warm up to ambient temperature over 30 min. Aqueous sodium sulfite and ethyl acetate were added and the organic layer was separated, washed with water and concentrated in vacuo. The residue was purified by column chromatography on silica gel and eluted with ethyl acetate: hexane (1:1) to give compound 3 as a solid: mp 117–19° C.; MS 484 (MH⁺).

EXAMPLE 4

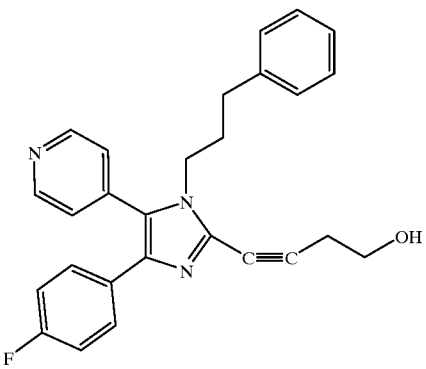

4-(4-Fluorophenyl)-2-(4-hydroxybutyn-1-yl)-1-(3-phenylpropyl)-5-(4-pyridyl)imidazole Cpd. 4

Triethylamine (80 mL), bis(acetato)bis(triphenylphosphine)palladium II ((0.71 g, 0.95 mmol) and 3-butyn-1-ol (2.90 mL, 37.6 mmol) were added to a solution of compound 3 (9.10 g, 18.8 mmol) in methylene chloride (40 mL). The reaction mixture was stirred at reflux for 4 h, concentrated in vacuo and partitioned between H₂O and ethyl acetate. The organic layer was concentrated in vacuo and purified by column chromotography using ethyl acetate as an eluent to give compound 4 as a solid: mp 125–26.5° C.; MS 426 (MH+).

Aside from compound 4, additional compounds of Formula I were prepared by the method of this example. Appropriately substituted ethynyl derivatives were used in place of 3-butyn-1-ol to give the compounds listed in Table D with their found mass spectrum data.

TABLE D

| Cpd. | R$_1$ | R$_2$ | R$_3$ | R$_4$ | (MH+) |
|---|---|---|---|---|---|
| 34 | 4-F-Ph | 4-pyr | (CH$_2$)$_3$Ph | C(C)(CH$_2$)$_2$CH$_3$ | 424 |
| 35 | 4-F-Ph | 4-pyr | (CH$_2$)$_3$Ph | C(C)(CH$_2$)$_3$OH | 440 |
| 36 | 4-F-Ph | 4-pyr | (CH$_2$)$_3$Ph | C(C)(CH$_2$)$_3$CN | 449 |
| 38 | 4-F-Ph | 4-pyr | (CH$_2$)$_3$Ph | C(C)(CH$_2$)$_3$Ph | 500 |
| 39 | 4-F-Ph | 4-pyr | (CH$_2$)$_3$Ph | C(C)(CH$_2$S(CH$_2$)CH$_3$ | 512 |
| 41 | 4-F-Ph | 4-pyr | (CH$_2$)$_3$Ph | C(C)(CH$_2$)$_5$CH$_3$ | 466 |
| 42 | 4-F-Ph | 4-pyr | (CH$_2$)$_3$Ph | C(C)(CH$_2$)$_4$OH | 454 |
| 43 | 4-F-Ph | 4-pyr | (CH$_2$)$_3$Ph | C(C)(CH$_2$cyclopentyl | 464 |
| 47 | 4-F-Ph | 4-pyr | (CH$_2$)$_3$Ph | C(C)(CH$_2$)OH | 412 |
| 48 | 4-F-Ph | 4-pyr | (CH$_2$)$_3$Ph | C(C)(CH$_2$)OPHT | 557 |

EXAMPLE 5

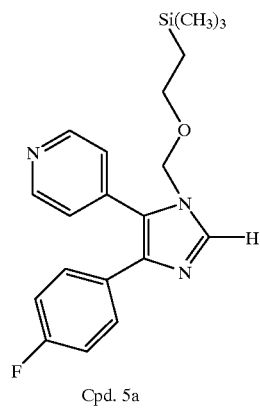

Cpd. 5a

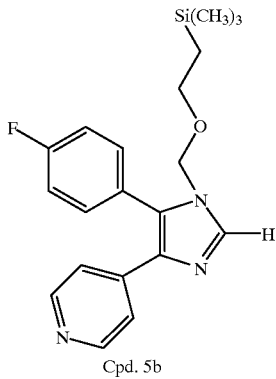

Cpd. 5b 4-(4-Fluorophenyl)-5-(4-pyridyl)-1-(2-(trimethylsilyl)ethoxymethyl)-imidazole Cpd. 5a 5-(4-Fluorophenyl)-4-(4-pyridyl)-1-(2-(trimethylsilyl) ethoxymethyl)-imidazole Cpd. 5b 60% Sodium Hydride (0.92 g, 23 mmol) was added to a stirred solution of 5(4)-(4-fluorophenyl)-4(5)-(4-pyridyl)-imidazole (5.50 g, 23 mmol) in DMF under N$_2$. 2-(Trimethylsilyl)ethoxymethyl chloride (4.07 mL, 23 mmol) was added after 15 min and the resulting mixture was stirred for 3 h, poured into H$_2$O, dried (MgSO$_4$) and concentrated in vacuo. The resulting oil was purified by column chromatography on silica gel using ethyl acetate as an eluent. The first isomer crystallized to give compound 5a: mp 111–13 ° C.; MS 370 (MH+). The second isomer crystallized to give compound 5b: mp 62–64° C.; MS 370 (MH+).

EXAMPLE 6

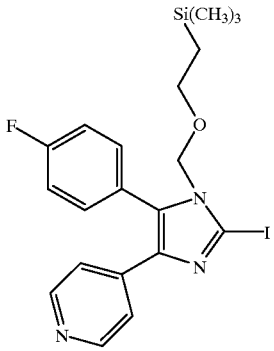

5-(4-Fluorophenyl)-2-iodo-4-(4-pyridyl)-1-(2-(trimethylsilyl)ethoxymethyl)-imidazole Cpd. 6

2N n-Butyllithium/THF (3.2 mL) was added to a stirred solution of compound 5b (2.35 g, 6.40 mmol) in ether (150 mL) at −78° C. After 1 h, iodine (2.16 g, 8.50 mmol) was added and the reaction mixture was stirred at ambient temperature for 1 h. Aqueous sodium sulfite (100 mL) was added and the resulting organic layer was washed with H$_2$O, dried (MgSO$_4$) and purified by column chromatography to give compound 6 as an oil: MS 496 (MH+).

EXAMPLE 7

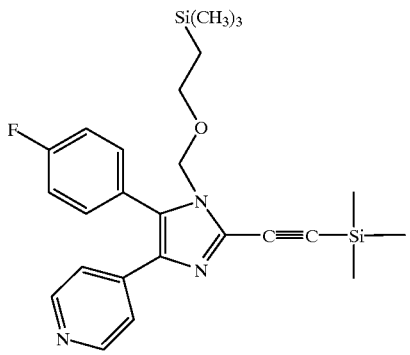

5-(4-Fluorophenyl)-4-(4-pyridyl)-2-(trimethylsilyl) ethinyl-1-(2-(trimethylsilyl)ethoxymethyl)-imidazole Cpd. 7

Trimethylsilylacetylene (0.31 mL), bis(acetato)bis (triphenylphosphine)-palladium (II) (5 mol %) were added to a solution of compound 2 (0.60 g, 1.20 mmol) in triethylamine (15 mL) and the resulting mixture was stirred at 70° C. for 18 h. The resulting mixture was cooled to room temperature, and the solid filtrate was isolated. This solid was washed with triethylamine and the combined organic layers were concentrated in vacuo. The residue was purified by column chromatography using ethyl acetate:hexane (1:1)

EXAMPLE 8

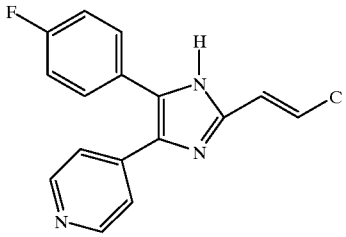

2-(2-Chlorovinyl)-5-(4-fluorophenyl)4-(4-pyridyl)-imidazole

Cpd. 8

3N HCl was added to a solution of compound 7 in ethanol and the mixture was heated at reflux for 5 h. The resulting reaction brew was concentrated in vacuo, neutralized with sodium bicarbonate and extracted with ethyl acetate. The organic layer was concentrated in vacuo and purified by column chromatography using ethyl acetate as an eluent to give compound 8 as a solid: mp 185–87° C.; MS 300 (MH$^+$).

EXAMPLE 9

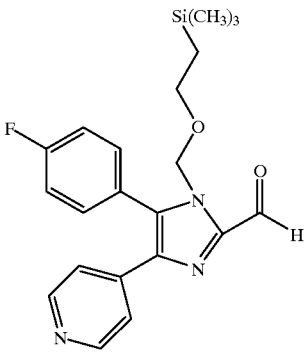

5-(4-Fluorophenyl)4-(4-pyridyl)-1-(2-(trimethylsilyl)ethoxymethyl)-imidazole-2-carboxaldehyde Cpd. 9

1.6 N n-BuLi (13 mL, 21 mmol) was added to a stirred solution of compound 5b (7.10 g, 19.2 mmol) in THF at −78° C. After 15 min, DMF (2.0 mL, 26 mmol) was added and the mixture was stirred at ambient temperature for 1 h and quenched with water. This mixture was extracted with ethyl acetate and the combined organic extracts were concentrated in vacuo. The residue was purified by column chromatography on silica gel using ethyl acetate: hexanes (1:1) to give compound 9 as a solid: mp 42–45° C.; MS 398 (MH$^+$).

EXAMPLE 10

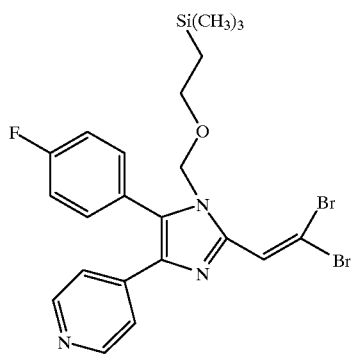

2-[2,2-Dibromoethylene-1-yl]-5-(4-fluorophenyl)4-(4-pyridyl)-1-(2-(trimethylsilyl)ethoxymethyl)imidazole Cpd. 10

Triphenyl phosphine (13.40 g, 51.1 mmol) was dissolved in methylene chloride (300 mL) and cooled to −10° C. A solution of carbon tetrabromide (8.50 g, 25.6 mmol) was added dropwise, followed by a solution of compound 9 (6.85 g, 17.2 mmol) and triethylamine (2.79 mL. 20 mmol) in methylene chloride. This mixture was stirred for 30 min, poured into ether (500 mL) and filtered. The filtrate was concentrated in vacuo purified by column chromatography on silica gel using ethyl acetate: hexane (1:1) as an eluent to give compound 10 as a solid: mp 128–31° C.; MS 554 (MH$^+$).

EXAMPLE 11

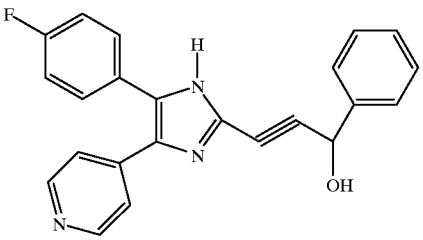

5(4)-(4-Fluorophenyl)-2-(3-hydroxy-3-phenyl-propyn-1 -yl)-4(5)-(4-pyridyl)imidazole Cpd. 11

1.6N n-Butyllithium (5.0 mL, 8.0 mmol) was added to a stirred solution of compound 10 (2.20 g, 3.80 mmol) in THF (50 mL) at −78° C. After 30 min benzaldehyde (0.40 mL, 3.94 mmol) was added and the mixture was allowed to stir at ambient temperature for 30 min. Water was added and the resulting organic layer was concentrated in vacuo and dissolved in MeOH (20 mL) and 1N HCl (20 mL). This mixture was stirred for 2 h at 50° C. and the resulting mixture was neutralized with sodium bicarbonate and extracted with ethyl acetate. The combined organic layer was dried (MgSO$_4$) and purified on silica gel using ethyl acetate as an eluent to give compound 11 as a solid: mp 193–94° C.; MS 370 (MH$^+$).

EXAMPLE 12

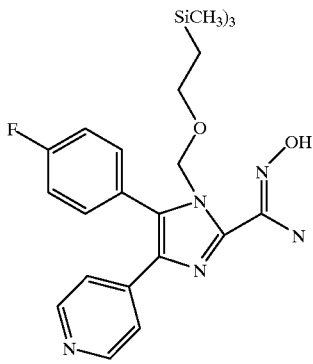

5-(4-Fluorophenyl)-4-(4-pyridyl)-1-(2-(trimethylsilyl)ethoxymethyl)-2-oximinoimidazole Cpd. 12

A solution of hydroxylamine hydrochloride (0.09 g, 1.3 mmol), sodium bicarbonate (0.11 g, 1.3 mmol) and H$_2$O (5 mL) was added to a stirred solution of compound 9 (0.50 g, 1.2 mmol) in MeOH (5 mL) at room temperature. This mixture was stirred for 3 h and poured into H$_2$O. The solid precipitate was filtered and dried in vacuo to give the title compound as a solid: mp 212–13° C.; MS 413 (MH$^+$).

EXAMPLE 13

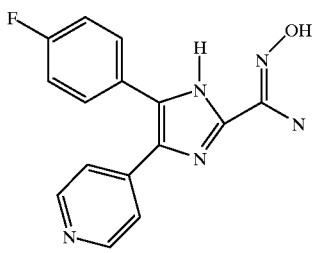

5-(4-Fluorophenyl)-4-(4-pyridyl)-2-imidazoleoxime

Cpd. 13

0.5 M HCl (3 mL) was added to a solution of compound 12 in MeOH (5 mL). This mixture was heated at reflux for 2 h, neutralized with sodium bicarbonate and the resulting precipitate was filtered. This solid was recrystallized form MeOH/H$_2$O to give the title compound as a solid; mp 318–20° C.; MS 283 (MH$^+$).

EXAMPLE 14

2-(5-Chloropentyn-1-yl)4-(4-fluorophenyl)-1-(3-phenylpropyl)-5-(4-pyridyl)imidazole Cpd. 14

Triethylamine (50 mL), bis(acetato)bis(triphenylphosphine)palladium II (0.71 g, 0.95 mmol) and 5-chloro-1-pentyne (0.71 mL, 6.70 mmol) and compound 3 (1.62 g, 3.35 mmol) were stirred at reflux for 16 h. Ethyl acetate was added and the solid precipitates were removed by filtration The filtrate layer concentrated in vacuo and purified by column chromatography using ethyl acetate-hexane (1:2) as an eluent to give compound 14 as a solid: mp 102–104° C.

EXAMPLE 15

4-(4-Fluorophenyl)-2-(4-N-phenylcarbamoyloxybutyn-1-yl)-1-(3-phenylpropyl)-5-(4-pyridyl)imidazole Cpd 15

Phenylsiocyanate (11 mL, 1.0 mmol) was added to a stirred solution of compound 4 (200 mg, 0.50 mmol) in pyridine. The mixture was stirred for 4 h and poured into ice. The solid precipitate was washed with water and dried to give compound 15 as a solid: mp 120–24° C.

EXAMPLE 16

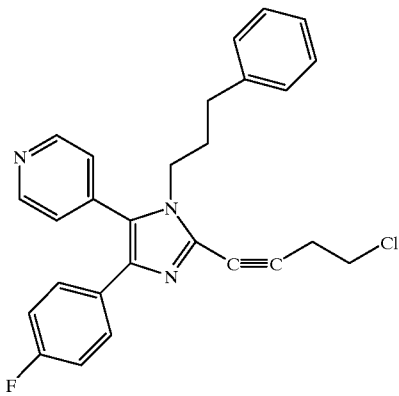

2-(4-Chlorobutyn-1-yl)4-(4-fluorophenyl)-1-(3-phenylpropyl)-5-(4-pyridyl)imidazole Cpd.16

Triphenylphosphine (1.11 g, 4.23 mmol) and carbon tetrachloride (0.41 mL, 4.23 mmol) were added to a solution of compound 4 (0.9 g, 2.12 mmol) at room temperature. The mixture was stirred for 22 h, concentrated in vacuo and purified by column chromatography using ethyl acetate: hexane (1:1) as an eluent to give the title compound as a solid: mp 132–34° C.

EXAMPLE 17

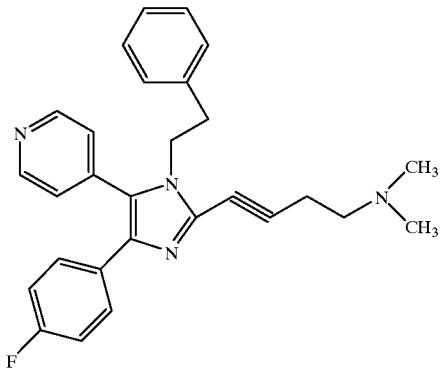

2-(4-Dimethylaminobutyn-1-yl)4-(4-fluorophenyl)-1-(3-phenylpropyl)-5-(4-pyridyl)imidazole Cpd. 17

A solution of compound 16 (208 mg, 0.47 mmol) in 2N dimethylamine/MeOH (10 mL) was stirred for 18 h at room temperature and concentrated in vacuo. The residue was purified by column chromatography using methylene chloride: MeOH (19:1) as an eluent to give the title compound as a solid: mp 115–17° C.

What is claimed is:

1. A compound of Formula I

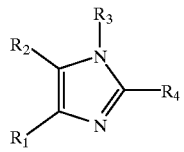

wherein:
$R_1$ is phenyl, substituted phenyl where the substituents are selected from the group consisting of $C_{1-5}$alkyl, halogen, nitro, trifluoromethyl, and nitrile, or pyridinyl;

$R_2$ is phenyl, substituted phenyl where the substituents are selected from the group consisting of $C_{1-5}$alkyl, halogen, nitro, trifluoromethyl, and nitrile or pyridinyl where the pyridinyl is optionally $C_{1-4}$alkyl substituted;

$R_3$ is hydrogen, SEM, $C_{1-5}$alkoxycarbonyl, aryloxycarbonyl, aryl$C_{1-5}$-alkyloxycarbonyl, aryl$C_{1-5}$alkyl, substituted aryl$C_{1-5}$alkyl where the aryl substituents are independently selected from one or more members of the group consisting of $C_{1-5}$alkyl, $C_{1-5}$alkoxy, halogen, amino, $C_{1-5}$alkylamino, and di$C_{1-5}$alkylamino, phthalimido$C_{1-5}$-alkyl, amino$C_{1-5}$alkyl, diamino$C_{1-5}$alkyl, succinimido$C_{1-5}$alkyl, $C_{1-5}$alkylcarbonyl, arylcarbonyl, $C_{1-5}$alkylcarbonyl$C_{1-5}$alkyl, aryloxycarbonyl$C_{1-5}$alkyl;

$R_4$ is (A)—(CH$_2$)$_q$—X where:
A is vinylene, ethynylene or

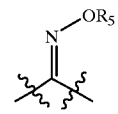

where
$R_5$ is selected from the group consisting of hydrogen, $C_{1-5}$alkyl, phenyl and phenyl$C_{1-5}$alkyl;
q is 0–9;
X is selected from the group consisting of hydrogen, hydroxy, vinyl, substituted vinyl where one or more substituents are selected from the group consisting of fluorine, bromine, chlorine and iodine), ethynyl, substituted ethynyl (where the substituents are selected from one or more of the group consisting of fluorine, bromine chlorine and iodine, $C_{1-5}$alkyl, substituted $C_{1-5}$alkyl where the alkyl substituents are selected from the group consisting of one or more $C_{1-5}$alkoxy trihaloalkyl, phthalimido and amino, $C_{3-7}$cycloalkyl, $C_{1-5}$alkoxy, substituted $C_{1-5}$alkoxy where the alkyl substituents are selected from the group consisting of phthalimido and amino, phthalimidooxy, phenoxy, substituted phenoxy (where the phenyl substituents are selected from the group consisting of $C_{1-5}$alkyl, halogen and $C_{1-5}$alkoxy), phenyl, substituted phenyl where the phenyl substituents are selected from the group consisting of $C_{1-5}$alkyl, halogen and $C_{1-5}$alkoxy, aryl$C_{1-5}$alkyl, substituted aryl$C_{1-5}$alkyl where the aryl substituents are selected from the group consisting of $C_{1-5}$alkyl, halogen and $C_{1-5}$alkoxy, arylhydroxy$C_{1-5}$alkyl amino, $C_{1-5}$alkylamino, di$C_{1-5}$alkylamino, nitrile, oxime, benxyloxyimino, $C_{1-5}$alkyloxyimino, phthalimido, succinimido, $C_{1-5}$alkylcarbonyloxy, phenylcarbonyloxy, substituted phenylcarbonyloxy where the phenyl substitutents are selected from the group consisting of $C_{1-5}$alkyl, halogen and $C_{1-5}$alkoxy, phenyl$C_{1-5}$alkylcarbonyloxy, where the phenyl substituents are selected from the group consisting of $C_{1-5}$alkyl, halogen and $C_{1-5}$alkoxy, aminocarbonyloxy, $C_{1-5}$alkylaminocarbonyloxy, di$C_{1-5}$alkylaminocarbonyloxy, $C_{1-5}$alkoxycarbonyloxy, substituted $C_{1-5}$alkoxycarbonyloxy where the alkyl substituents are selected from the group consisting of methyl, ethyl, isopropyl and hexyl, phenoxycarbonyloxy, substituted phenoxycarbonyloxy where the phenyl substituents are selected from the group consisting of $C_{1-5}$alkyl, $C_{1-5}$alkoxy, and halogen, $C_{1-5}$alkylthio, substituted $C_{1-5}$alkylthio where the alkyl substituents are selected from the group consisting of hydroxy and phthalimido, $C_{1-5}$ alkylsulfonyl, phenylsulfonyl, substituted phenylsulfonyl where the phenyl substituents are selected from the group consisting of bromine, fluorine, chloride, $C_{1-5}$alkoxy and trifluoromethyl; with the proviso:

if A is

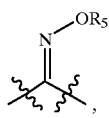

q is 0 and X is H, $R_3$ may not be SEM;
and pharmaceutically acceptable salts thereof.

2. The compound of claim 1 where $R_1$ is substituted phenyl and $R_2$ is pyridin-2-yl, pyridin-3-yl or pyridin-4-yl.

3. The compound of claim 2 where $R_1$ is 4-fluorophenyl and $R_2$ is pyridin-4-yl.

4. The compound of claim 3 where $R_3$ is hydrogen, aryl$C_{1-5}$alkyl, or substituted aryl$C_{1-5}$alkyl.

5. The compound of claim 4 where $R_3$ is hydrogen or phenyl$C_{1-5}$alkyl.

6. The compound of claim 5 where A is ethynylene and q is 0–5.

7. The compound of claim 6 where X is succinimido, hydroxy, methyl, phenyl, $C_{1-5}$alkylsulfonyl, $C_{3-6}$-cycloalkyl, $C_{1-5}$alkylcarbonyloxy, $C_{1-5}$alkoxy, phenylcarbonyloxy, $C_{1-5}$alkylamino, di$C_{1-5}$alkylamino, or nitrile.

8. A compound and pharmaceutically acceptable salts thereof selected from the group consisting of 4-(4-fluorophenyl)-2-(4-hydroxybutyn-1-yl)-1-(3-phenylpropyl)-5-(4-pyridinyl)imidazole, 4-(4-fluorophenyl)-2-(3-hydroxypropyn-1-yl)-1-(3-phenylpropyl)-5-(4-pyridinyl)imidazole, 4(4-fluorophenyl)-2-(5-hydroxypentyn-1-yl)-1-(3-phenylpropyl)-5-(4-pyridinyl)imidazole, and 4-(4-fluorophenyl)-2-(6-hydroxyhexyn-1-yl)-1-(3-phenylpropyl)-5-(4-pyridinyl)imidazole.

9. A compound 4-(4-fluorophenyl)-2-(4-hydroxybutyn-1-yl)-1-(3-phenylpropyl)-5-(4-pyridinyl)imidazole and pharmaceutically acceptable salts thereof.

10. A compound and pharmaceutically acceptable salts thereof selected from the group consisting of 4-(4-fluorophenyl)-2-(5-cyanopentyn-1-yl)-1-(3-phenylpropyl)-5-(4-pyridinyl)imidazole, 4-(4-fluorophenyl)-2-(4-dimethylaminobutyn-1-yl)-1-(3-phenylpropyl)-5-(4-pyridinyl)imidazole, 4-(4-fluorophenyl)-2-(4-(phenylcarbonyloxy)butyn-1-yl)-1-(3-phenylpropyl)-5-(4-pyridinyl)imidazole, 4-(4-fluorophenyl)-2-(4-methylcarbonyloxy)butyn-1-yl)-1-(3-phenylpropyl)-5-(4-pyridinyl)imidazole, 4-(4-fluorophenyl)-2-(3-cyclopentylpropyn-1-yl)-1-(3-phenylpropyl)-5-(4-pyridinyl)imidazole, and 4-(4-fluorophenyl)-2-(5-(butylsulfonyl)pentyn-1-yl)-1-(3-phenylpropyl)-5-(4-pyridinyl)imidazole.

11. A compound and pharmaceutically acceptable salts thereof selected from the group consisting of 4-(4-fluorophenyl)-2-(octyn-1-yl)-1-(3-phenylpropyl)-5-(4-pyridinyl)imidazole, 4-(4-fluorophenyl)-2-(5-butylthiopentyn-1-yl)-1-(3-phenylpropyl)-5-(4-pyridinyl)imidazole, 4-(4-fluorophenyl)-2-(5-phenylpentyn-1-yl)-1-(3-phenylpropyl)-5-(4-pyridinyl)imidazole, 4-(4-fluorophenyl-2-(5-chloropentyn-1-yl)-1-(3-phenylpropyl)-5-(4-pyridinyl)imidazole, 4-(4-fluorophenyl)-2-(5-hydroxypentyn-1-yl)-1-(3-phthalimidolpropyl)-5-(4-pyridinyl)imidazole, 4-(4-fluorophenyl-2-(pentyn-1-yl)-1-(3-phenylpropyl)-5-(4-pyridinyl)imidazole, and 4-(4-fluorophenyl)-2-(5-N-succinimidopentyn-1-yl)-1-(3-phenylpropyl)-5-(4-pyridinyl)imidazole.

12. The compound of claim 1 where $R_1$ is phenyl and $R_2$ is selected from the group consisting of pyridin-2-yl, pyridin-3-yl and pyridin-4-yl.

13. The compound of claim 12 where $R_2$ is pyridin-3-yl.

14. A pharmaceutical composition comprising a compound according to claim 1 and a pharmaceutically acceptable carrier or diluent.

15. A pharmaceutical composition comprising a compound according to claim 7 and a pharmaceutically acceptable carrier or diluent.

16. A pharmaceutical composition comprising a compound according to claim 8 and a pharmaceutically acceptable carrier or diluent.

17. A pharmaceutical composition comprising a compound according to claim 9 and a pharmaceutically acceptable carrier or diluent.

* * * * *

UNITED STATES PATENT AND TRADEMARK OFFICE
CERTIFICATE OF CORRECTION

PATENT NO. : 5,965,583
DATED : October 12, 1999
INVENTOR(S) : Beers et al.

It is certified that error appears in the above-identified patent and that said Letters Patent is hereby corrected as shown below:

Title,
Kindly replace the last word "DISEASE" with -- DISEASES --.

Signed and Sealed this

Twenty-seventh Day of November, 2001

Attest:

NICHOLAS P. GODICI
Attesting Officer     Acting Director of the United States Patent and Trademark Office